United States Patent [19]

Lanning

[11] Patent Number: 4,586,924
[45] Date of Patent: May 6, 1986

[54] VEIN CONSTRICTOR AND IMMOBILIZER

[76] Inventor: Charles T. Lanning, P.O. Box 323, Watertown, S. Dak. 57201

[21] Appl. No.: 629,169

[22] Filed: Jul. 9, 1984

[51] Int. Cl.$^4$ .............................................. A61M 5/00
[52] U.S. Cl. ..................................... 604/115; 128/133
[58] Field of Search ................. 604/115; 128/325, 327, 128/DIG. 6, 133

[56] References Cited

U.S. PATENT DOCUMENTS

| 812,679 | 2/1906 | Reimanns | 128/341 |
|---|---|---|---|
| 1,561,116 | 11/1925 | Silliman | 604/115 |
| 1,824,516 | 9/1931 | Tyvand | 604/115 X |
| 2,103,174 | 12/1937 | Posada | 604/115 |
| 3,324,854 | 6/1967 | Weese | . |
| 4,196,735 | 4/1980 | Ayer | 604/115 |
| 4,316,461 | 2/1982 | Marais et al. | 128/133 |
| 4,332,248 | 6/1982 | DeVitis | 128/133 X |

FOREIGN PATENT DOCUMENTS 1003251  11/1951  France ................................ 128/133

Primary Examiner—Stephen C. Pellegrino
Attorney, Agent, or Firm—Palmatier & Sjoquist

[57] ABSTRACT

A vein constrictor and immobilizer device comprising a pressure plate and a pressure means. The plate has a top pressure face and a bottom engaging face. Both faces are substantially flat. In one end of the plate is a notch through the plate's thickness. A groove is in the bottom face starting at the inner end of the notch and terminating intermediate the notch and opposing edge of the bottom engaging face. An attached ring-like handling structure pressure means is mounted on the top face for applying pressure on the plate to bring the bottom face to bear firmly on the flesh of a arm or leg to thereby constrict a vein and immobilize the vein in the notch and groove for needle insertion.

4 Claims, 13 Drawing Figures

VEIN CONSTRICTOR AND IMMOBILIZER

BACKGROUND OF THE INVENTION

The present invention relates to an improved device to aid in holding a vein stable when inserting a needle into the vein for drawing blood or administering drugs.

Veinal blood flow is only towards the heart. Within the veins are leaflet valves which allow blood flow in this direction and stop its reverse flow. When inserting a needle into the vein, typically a tourniquet is positioned on an extremity such as an arm or leg. The veinal blood flow is thereby halted or constricted and the veins on the hand or foot side of the tourniquet begin to swell or distend becoming quite defined and noticeable. Once the desired vein for penetration has been selected, the operator pierces the vein with the needle tip.

The problems encountered with veinal penetration are widely known: the vein may be missed altogether; the needle may completely penetrate through the entire vein; and unsuccessful penetration efforts may injure or damage the vein or surrounding tissue—all to the pain and injury of the patient. After a tourniquet has been applied on an arm, the veins in the extremity become somewhat inflexible. The veins however, still remain measurably resilient to thwart even an experienced operator's attempt at needle insertion. Essentially, any exerted pressure by a needle tip, not longitudinally aligned with a distended vein, may cause the vein to move and resist a piercing attempt.

In the past, known efforts at successful veinal penetration have dealt with using a form of a tourniquet about the arm or leg and some form of an immobilizing means about the vein to be pierced. The operator may attempt to hold the vein between two fingers striving to keep it stationary and thus avoid painful and injurious false efforts in piercing the vein.

Various bulkly and cumbersome instruments have also been utilized in attempting to immobilize the vein for longitudinal needle insertion. U.S. Pat. No. 1,561,116, issued to Silliman on Nov. 10, 1925, is a hand held vein stabilizer for placing over a vein having a flat metal plate including a notch to be directed towards the heart. U.S. Pat. No. 1,824,516, granted to Tyvand on Sept. 22, 1931, is a vein retainer comprising a complex plate structure to be placed over a vein and held there by a tourniquet. U.S. Pat No. 2,103,174, issued to Posada on Dec. 21, 1937, is a surgical instrument having a tourniquet band and a plate, which is attached to the band's end. A central opening is in the plate for retaining a vein. U.S. Pat. No. 3,324,854, granted to Weese on June 13, 1967, is a device to be attached to the barrel of a syringe to stabilize a vein. Such instruments have helped prevent transverse movement of the vein but manifest various limitations in their ease of operation, release and success.

SUMMARY OF THE INVENTION

The present invention provides an improved device to constrict and immobilize a vein in an extremity, such as arm or leg, so that a needle may be easily inserted into the vein. The invention provides for the quick and reliable constriction, distension and immobilization of the vein. The effort of locating the upper, peripheral surface of the vein for piercing and the vein's central axial region for operably positioning the needle tip have been made easier.

The invention has a pressure plate to be laid on the arm or leg. It has a top pressure face and a bottom engaging face. The bottom face is substantially flat. Various suitable pressure means for engaging the device, such as an attached ring-like handling structure or a tourniquet, may be used on the plate's top face to bring the bottom face to bear firmly on the flesh of the arm or leg. In one end of the plate is a slot or notch through the plate's thickness. A groove, in the bottom face, starts at the inner end of the notch and has a closed end intermediate the notch and opposing edge of the bottom face. The groove may be broadened or deepened at its closed end to allow greater distension of the vein for easy needle insertion into the bore of the vein.

The pressure plate is initially placed over the arm or leg, preferably with the notch pointing toward the extremity. The groove and notch are then aligned over the desired vein to be pierced. Upon applying gentle pressure on the top face, the veinal blood flow is halted or constricted. The flat surface of the bottom face, adjacent the groove's closed end, is the primary veinal flow barrier. That is, the vein in the groove itself is not collapsed. Rather, the vein collapses at the groove's closed end.

As the vein distends, the groove conforms the shape of the upper periphery of the vein to its surface. The vein also begins to rise into the notch. The notch and groove therefore, cooperatively immobilize and shape the distending vein in preparation for insertion of the needle. The operator then simply pierces the vein with the needle in the notch region of the plate in the direction of the groove.

For veins that are hard to locate, a tourniquet or some variation thereof, must be used. The present invention will aid a tourniquet in constricting, distending and immobilizing these hard to locate veins. Conversely, some veins are already partially distended and quite indentifiable so that little constriction, if any, is needed. The disclosed invention provides a ring-like handling structure attached to the top face. The ring structure provides for a finger or thumb to be inserted therein and effectively manipulate the pressure plate over the vein. The finger or thumb can then provide the adequate downward pressure or force to sufficiently distend, immobilize and shape one of these easy-to-locate veins for insertion of a needle.

An advantageous vein constrictor and immobilizer device for needle insertion is disclosed. The device is quick and easy to engage and release thereby shortening the time for the needle to be inserted and operate. The device's construction is simple, lightweight and inexpensive, as to be disposable. It also may be made of such material so that it may be reuseable.

The invention further provides a novel notch and groove arrangement that cooperatively provides an additional immobilized length of distended vein for needle insertion up to the groove's closed end while under a gentle pressure from above.

An especially preferred feature of the invention is the novel groove on its bottom face. The groove provides for exact immobilization and conformation of a ballooning vein. In other words, the distending vein's upper periphery raises and conforms to the surface of the groove for its fixation so that the operator may make a safe and effortless needle insertion into the vein's bore after piercing the vein.

DETAILED SPECIFICATION

Figure 8:
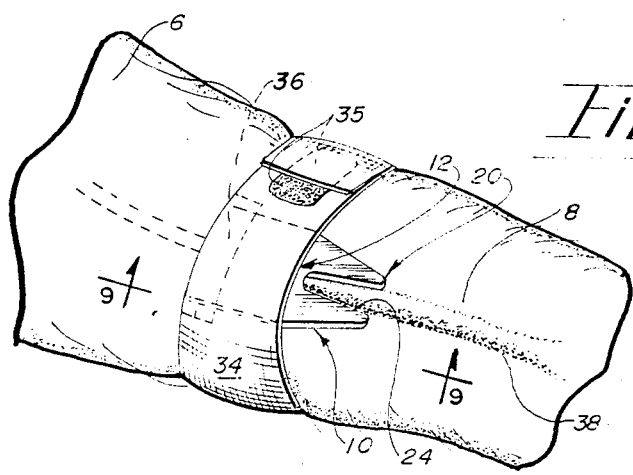
FIG. 8 is a perspective view of a modified form of the invention shown applied to a person's arm.
Figure 1:
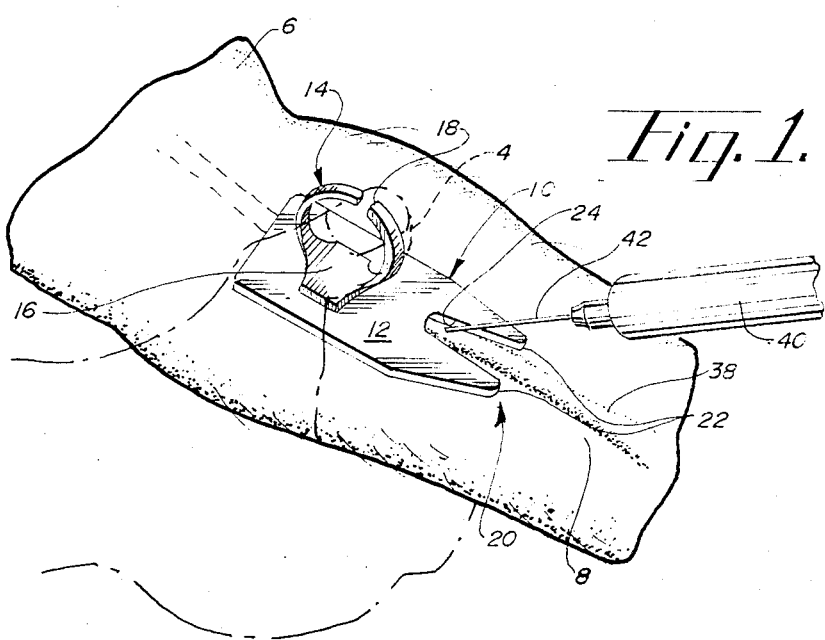
FIG. 1 is a perspective view of the vein consrictor and immobilizer device in operable position over a vein on an arm with a thumb in broken outline in an attached ring-like handling structure.

Referring to FIGS. 1-5 and 13, the pressure plate of the vein constrictor and immobilizer, generally indicated by numeral 10, is made of a suitably rigid material. Should the pressure plate be desired to be disposable after its use, material such as an inexpensive plastic may be used. If the pressure plate is to be reused, a suitably more durable material, such as metal may be used that is capable of withstanding multiple sterilizations.

The pressure plate's 10 dimensions may vary according to its particular applications. That is, larger for larger veins, smaller for smaller veins, such as thoses which vary between adults, children or animals. The disclosed preferred embodiment is approximately 1 and ¾ inches in length, 1 inch in width and ⅛ inch in thickness.

Plate 10 has a top pressure face 12 preferably flat across portions of its width and a bottom engaging face 26, which is also flat. Plate 10 has a tapered end 20 opposite the top face 12. At tapered end 20 there is a pair of prongs, fingers or points 22 which define tapered end 20. Between points 22 there is a slot or notch 24. Notch 24 extends endwise and through the plate's 10 thickness. In bottom face 26 an elongated groove 28, semicircular in cross section, begins at the inner end of notch 24 and extends substantially in longitudinal alignment with notch 24. Groove 28 terminates in bottom face 26 intermediate the notch 24 and opposing edge 25 of bottom face 26 at closed end 30. Bottom face 26 has adjacent flat surfaces 29 about the groove's 28 closed end 30.

Plate 10 has a ring-like handling structure 14 for exerting a downward force on the top pressure face 12. Ring structure 14 has a flat base 16 for suitably mounting on top face 12. However, ring structure 14 may be formed integral with plate 10. Ring 14 is open at 18.

Tapered end 20 visually aids in the initial orientation of plate 10 as visible points 22 are directed away from the heart and toward the hand or foot. Tapered end 20 also conserves material used in the plate's 10 construction.

Notch 24 provides for a stay or immobilization for a distending vein 38 and thereby prevents any transverse movement during needle insertion.

Groove 28 is preferably semicircular in cross section to accommodate the tubular configuration of a distending vein 38. While notch 24 allows the ballooning vein 38 to rise upward and be held stationary, groove 28 conforms the upper periphery of the distending vein to the surface of groove 28. After initial needle penetration of the vein 38 in the notch 24 region, the operator further inserts needle tip 42 to its desired length by aiming just below the surface of groove 28. Groove 28 thereby provides an additional length of distended and immobilized vein.

Ring structure 14 provides for a finger or thumb 4 to be inserted therein for easy handling of plate 10 over vein 38. Quick release of plate 10 from the fleshy tissue 8 by lifting thumb 4 results in faster resumption of veinal blood flow which is necessary for the needle to function in blood withdrawal or drug administration. Therefore, the time in which the needle is inserted and operating within a vein has been shortened by this device. Ring 14 is also open at 18 for expansion and accommodation of large fingers. Plate 10, with the ring structure 14, may be aided by a conventional tourniquet when encountering difficulties in locating a vein for needle insertion.

This construction allows the flat surfaces 29 of bottom face 26, adjacent closed end 30, to constrict the veinal blood flow in vein 38 of arm 6 at closed end 30 while under gentle pressure from above by the ring structure 14.

Figure 6:
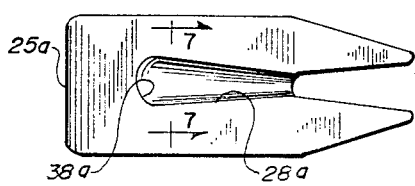
FIG. 6 is a bottom plan view of a modified form of the pressure plate.
Figure 7:
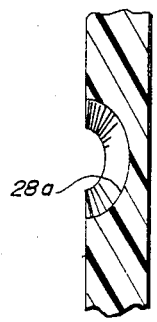
FIG. 7 is an enlarged detail cross sectional view taken along line 7—7 of FIG. 6.
Figure 10:
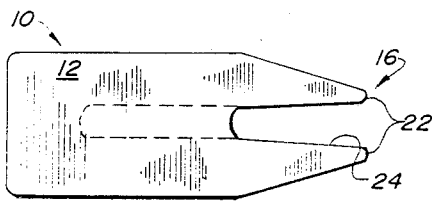
FIG. 10 is a top plan view of the pressure plate of FIGS. 8 and 9.
Figure 2:
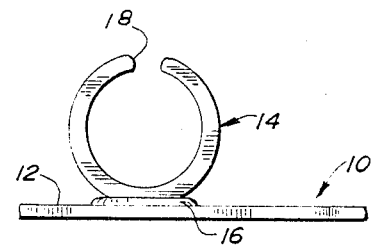
FIG. 2 is a side elevation of the invention of FIG. 1.
Figure 4:
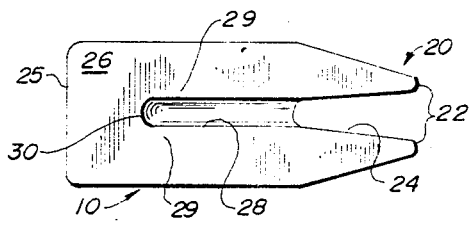
FIG. 4 is a bottom plan view of the pressure engaging face.
Figure 3:
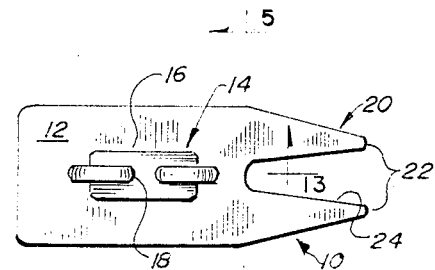
FIG. 3 is a top plan view of the device with the ring-like handling structure as shown in FIG. 1.

Referring to FIGS. 6 and 7, modified groove 28a is broadened or has an increasing depth towards its closed end 30a to allow for greater distension of the vein for easy needle insertion into the bore of a vein.

Figure 9:
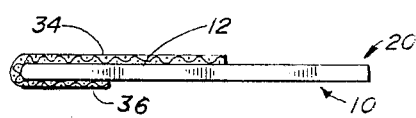
FIG. 9 is cross sectional view taken approximately at 9—9 of FIG. 8.
Figure 5:
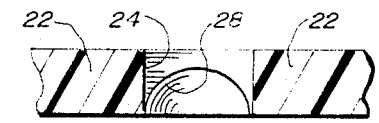
FIG. 5 is an enlarged detail cross sectional view taken along line 5—5 of FIG. 3.

When encountering veins that are difficult to locate, a modified form of the invention using tourniquet 34, as shown in FIGS. 8 and 9, may be used. Tourniquet 34, applied to top face 12, has suitable fastening means, such as velcro fastening pads 35. Tourniquet 34 has a pocket 36 which may be integrally formed with, or stitched onto, the underside of tourniquet 34 for holding plate 10 under tourniquet 34. Pocket 36 should not cover groove 28 or closed end 30. After the selected vein 38 has been pierced and the needle tip 42 inserted to its desired length, tourniquet 34 is released and pocket 36 advantageously carries plate 10 away with it. This release results in resumption of veinal blood flow necessary for the needle to function in blood withdrawal or drug administration.

Figure 11:
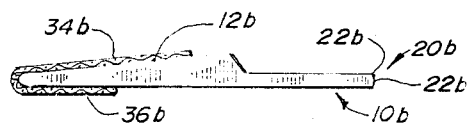
FIG. 11 is a cross sectional view of another variation of the invention.

In another construction of the pressure plate 10b, as shown in FIG. 11, top face portion 12b has an upward incline towards tapered end 20b or points 22b. Plate 10b may be inserted into pocket 36b on tourniquet 34b as similarly shown in FIGS. 8 and 9. When tourniquet 34b is gently tightened to constrict veinal blood flow, it exerts a force downward on inclinded top face 12b and points 22b will be further forced downward into the skin supplementally distending, shaping and immobilizing the vein. With this construction, the vein further balloons up into notch 24b for easier veinal penetration.

Figure 12:
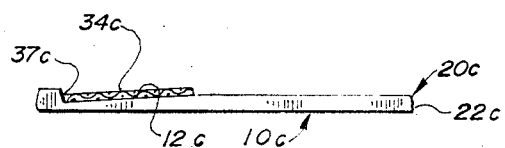
FIG. 12 is a cross sectional view of still another modified form of the invention.

In still another construction, as shown in FIG. 12, top face 12c has an indentation 37c across its width, opposite tapered end 20c. Indentation 37c provides a seat for tourniquet 34c and thereby holds plate 10c under tourniquet 34c. Top face 12c, beginning along indentation 37c, transversely inclines upwardly toward tapered end 20c so that points 22c will be further forced downward into the skin supplementally distending, shaping and immobilizing the vein. With this construction, the vein further balloons up into notch 24c for easier veinal penetration.

Figure 13:
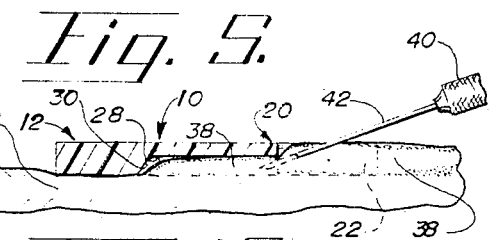
FIG. 13 is a detail cross sectional view taken at 13—13 of FIG. 3, shown applied to a person's arm.

In operation as shown in FIG. 13, pressure plate 10 of the vein constrictor and immobilizer is placed over fleshy tissue 8 of arm 6 and orientated over vein 38 with the tapered end 20 pointing away from the heart and towards the extremity. A pressure means, such as those previously described, is used to exert a gentle downward force on top pressure face 12 to halt or constrict the veinal blood flow at closed end 30. As the vein 38 distends, it comforts to the surface of groove 28 and balloons into notch 24 thereby becoming immobilized and ready for the veinal penetration by a hypodermic or intravenous syringe 40. The operator pierces the vein in the region of notch 24 and in the direction of the heart and groove 28. Piercing in this direction will allow groove 28 to provide an additional length of immobilized vein 38 helping the operator insert needle tip 42 to its desired length into vein 38.

The present invention may be embodied in other specific forms without departing from the spirit or essential attributes thereof. Therefore, the illustrated embodiments should be considered in all respects as illustrative and not restrictive, reference being made to the appended claims rather than to the foregoing description to indicate the scope of the invention.

That which is claimed is:

1. An improved vein constrictor and immobilizer that aids needle insertion into a vein, comprising
    (a) a rigid pressure plate including a top pressure face, an elongate notch extending endwise and through the plate's thickness, a substantially flat bottom face for engaging the skin above the vein to be penetrated, and an elongate groove in the bottom face beginning at the notch and said groove terminating intermediate said notch and opposing edge of said bottom face; and
    (b) a ring-like handling pressure means structure attached to said top face for insertion of a finger or thumb therein.

2. The device of claim 1, wherein the ring-like handling structure is broke open for allowing said ring to expand and accommodate various finger or thumb sizes.

3. The device of claim 1 wherein the notch has a closed end and an open end, and the notch is tapered divergently from the closed end to the open end.

4. The device of claim 3 wherein the plate has side edges extending along the notch, said edges tapering convergently with respect to each other toward the open end of the notch and defining pointed portions of the plate adjacent the open end of the notch.

* * * * *